United States Patent
Xu

(10) Patent No.: US 9,956,275 B2
(45) Date of Patent: May 1, 2018

(54) METHODS OF INHIBITING PLATELET AGGREGATION AND PREVENTING THROMBOSIS USING ANTIBODIES THAT BIND (NA⁺+K⁺)-ATPASE BETA SUBUNIT

(71) Applicant: Kai Yuan Xu, Cockeysville, MD (US)

(72) Inventor: Kai Yuan Xu, Cockeysville, MD (US)

(*) Notice: Subject to any disclaimer, the term of this patent is extended or adjusted under 35 U.S.C. 154(b) by 0 days. days.

(21) Appl. No.: 15/391,199

(22) Filed: Dec. 27, 2016

(65) Prior Publication Data
US 2017/0106062 A1    Apr. 20, 2017

Related U.S. Application Data

(60) Continuation-in-part of application No. 14/713,032, filed on May 15, 2015, now Pat. No. 9,527,923, which is a continuation-in-part of application No. 14/692,584, filed on Apr. 21, 2015, now Pat. No. 9,238,695, which is a division of application No. 13/359,723, filed on Jan. 27, 2012, now Pat. No. 9,040,046.

(60) Provisional application No. 61/437,719, filed on Jan. 31, 2011.

(51) Int. Cl.
*A61K 39/00* (2006.01)
*C07K 16/40* (2006.01)

(52) U.S. Cl.
CPC .......... *A61K 39/0005* (2013.01); *C07K 16/40* (2013.01); *A61K 2039/505* (2013.01); *A61K 2039/6081* (2013.01); *C07K 2317/34* (2013.01); *C07K 2317/75* (2013.01)

(58) Field of Classification Search
CPC .......... A61K 39/0005; A61K 2039/505; A61K 2039/6081; C07K 16/40; C07K 2317/34; C07K 2317/75
See application file for complete search history.

(56) References Cited

U.S. PATENT DOCUMENTS

| | | | |
|---|---|---|---|
| 6,187,344 B1 | 2/2001 | Eljamal et al. | |
| 9,040,046 B2 | 5/2015 | Xu | |
| 9,409,949 B2 | 8/2016 | Xu | |
| 9,527,923 B2 | 12/2016 | Xu | |
| 9,738,711 B2 | 8/2017 | Comb et al. | |
| 9,738,724 B2 | 8/2017 | Thanos et al. | |

OTHER PUBLICATIONS

Vickers, et. al., Hydrolysis of Biological Peptides by Human Angiotensin-converting Enzyme -related carboxypeptidase. J. Biol. Chemistry. 2002, 277:14838-14843.
Knight, et. al., A novel coumarin labelled peptide for sensitive continuous assays of the matrix metalloproteinases. FEBS letters. 1992, 296:263-266.
Farley. et. al., The amino acid sequence of a Fluorescein labeled peptide for active site of (Na,K)-ATPase. J. Biol. Chem. 1984, 259:9532-9535.
Futaki, et. al., Arginine rich peptides. J. Biol. Chem. 2001, 276:5836-5840.
Foerg, et. al., Metabolic cleavage and translocation efficiency of selected cell penetrating peptides: a comparative study . . . AAPS Journal. 2008, 10:349-359.
Vidal, et. al., Solid-Phase Synthesis and Cellular Localization of a C-and/or N-terminal Labeled Peptide. Journal of Peptide Science. 1996, 2:125-133.
Buss, J.E, Sefton, B.M., Direct identification of Palmitic Acid at the lipid attached to p21ras. Mol.and Cellular Biol. 1986, 1:116-122.
Kim K, -H. Seong, B. L. Peptide Amidation: Production of Peptide Hormones in vivo and in vitro. Biotechnol. Bioprocess Eng. 2001, 6:244-251.
Horton, D.A., et al., Exploring privileged structures: the combinatorial synthesis of cyclic peotides. J. Comp-Aided Mol. Des. 2002, 16:415-430.
Kates, S. A., et al. A novel, conventient, three-dimensional orthogonal strategy for solidphase synthesis of cyclic peptides. Tetrahedron Lett. 1993,34:1549-1552.
Baddiley, J., et al. A synthesis of alanine labeled with heavy carbon in the alpha position. J Biol Chem. 1949, 178:300-402.
Ott, H. Studies on the incorporation of S35-labeled amino acids into blood proteins. Nucl Med (Stuttg). 1963, 2:Suppl, 1:311-317.
Polofriz, L., et al. Radioactive carbon labeled amino acids of the krebs cycle. Bio Chim Farm. 1963, 102:624-626.
Hunter, T., Signaling—2000 and Beyond. Cell. 2000, 100:113-127.
Roberts, et. al., Phosphorylation of soybean nodulin26 on serine 262 enhances water permeability and is regulated developmentally . . . The Plant Cell. 2003, 5:981-991.
Huck W. T.S. et. al., Forced Peptide Synthesis under elastomeric stamps. Angew. Chem. 2004, 116:4286-4289.
Veronese, F. M. Peptide and protein PEGylation: a review of problems and solutions. Biomaterials. 2001, 22:405-417.
Rothbard et. al., Polyarginine enters cells more efficiently than other poly cationic homopolymers. J. Peptide Res. 2000, 56:318-325.
Hoheisel et. al., Hybridisation based DNA screening on peptide nucleic acid (PNA) oligomer arrays. Nucleic acid Research. 1997, 25:2792-2799.
Mercer, RW, et al., Rat-brain Na,K-ATPase beta-chain gene: primary structure, tissue-specific expression, and amplification in ouabain-res . . . Mol Cell Biol,1986, 6:3884-3890.
Yang-Feng TL, et al., Chromosomal localization of human Na+, K+-ATPase alpha- and beta-subunit genes. Genomics. 1988, 2:128-138.
Brown, TA, et al., Molecular cloning and sequence analysis of the (Na+ + K +)-ATPase beta subunit from dog kidney. BBA. 1987, 912:244-253.

(Continued)

*Primary Examiner* — Ruixiang Li

(57) ABSTRACT

Methods of inhibiting platelet activation and aggregation using peptide vaccine or antibodies that have binding specificity for the β subunit of the (Na⁺+K⁺)-ATPase are provided, along with methods for inhibiting or preventing thrombosis in a subject using such peptide vaccine or antibodies.

2 Claims, 8 Drawing Sheets

(56) References Cited

OTHER PUBLICATIONS

Ovchinnikov,YuA, et al., Pig kidney Na+,K+-ATPase. Primary structure and spatial organization. FEBS Lett. 1986, 201:237-245.
Wallace, R. J., Acetylation of peptides inhibits their degradation by rumen micro-organisms. British Journal of Nutrition. 1992, 68:365-372.
Selo, et. al., Preferential labeling of alpha-amino N-terminal groups in peptide by biotin: application to the detection of specific . . . J. Immunol. Methods. 1996, 199:127-138.
Howl, et. al., Fluorescent and biotinylated linear peptides as selective bifunctional ligands for V1a vasopressin receptor. Eur. J. Biochem.1993, 213:711-719.
Buranda, et. al. Peptide, antibodies and FRET on beads in flow cytometry: a model system using fluoresceinated and biotinylated β-endorphin. Cytometry.1991, 37:21-31.
Matsuzaki, et. al., Mechanism of Synergism between Antimicrobial Peptides Magainin 2 and PGLa. Biochem. 1998, 37:15144-15153.
Pecht, et. al., Specific Excitation Energy Transfer for Antibodies to Dansyl labeled. Antigen. Eur. J. Biochem. 1971, 19:368-371.
He, J. X., et al. An efficient strategy for the large-scale synthesis of head-to-tail cyclic peptides. Letters in Peptide science. 1994, 1:25-30.
Shinagawa R., et al. In vitro neurotoxicity of amyloid β-peptide cross-linked by transglutaminase. Cytotechnology. 1997, 23:77-85.
Urlaub, H., et al. Contact sites of peptide-oligoribonucleotide cross-links identified by a combination of peptide . . . Journal of Protein Chemistry. 1997, 16:375-383.
Kunkel, G. R., et al. Contact-site cross-linking agents. Mol Cell Biochem. 1981, 34:3-13.
Tweedy, N. B., et al. Structure and energetics of a non-proline cis-peptidyl linkage in a proline-202—alanine carbonic anhydrase II variant. Biochemistry.1993,32:10944-10949.
Hum, G., et al. Synthesis of non-peptidyl alpha, alpha-difluoromethlenephosphonic acids on a soluble polymer support. J Comb Chem. 2000, 2:234-242.
Tanaka, T., et al. Peptidyl linkers for protein heterodimerization catalyzed by microbial transglutaminase. Bioconjugate Chemistry. 2004,15:491-497.
Light, A., et al. Modification of a single disulfide bond in trypsinogen and the activation of the carboxymethyl derivative. J Biol Chem. 1969, 244:6289-6296.
Valenzuela, D., et al. Modification of specific lysine residues in *E. coli* methionyl-tRNA synthetase by crosslinking to *E. coli* formylmethioine tRNA. BBRC. 1984, 119:677-687.
Waterman, M. R. Effect of carbamidomethylation of cysteine residues G11(104) alpha on the properties of hemoglobin A. Biochim Biophys Acta. 1976,39:167-174.

SEQUENCE LISTING

<160> NUMBER OF SEQ ID NOS: 6

<210> SEQ ID NO 1
<211> LENGTH: 13
<212> TYPE: PRT
<213> ORGANISM: Rattus rattus

<400> SEQUENCE: 1

Lys Glu Arg Gly Glu Phe Asn His Glu Arg Gly Glu Arg
1               5                   10

<210> SEQ ID NO 2
<211> LENGTH: 13
<212> TYPE: PRT
<213> ORGANISM: Homo sapiens

<400> SEQUENCE: 2

Lys Glu Arg Gly Asp Phe Asn His Glu Arg Gly Glu Arg
1               5                   10

<210> SEQ ID NO 3
<211> LENGTH: 13
<212> TYPE: PRT
<213> ORGANISM: Rattus rattus

<400> SEQUENCE: 3

Arg Asp Glu Asp Lys Asp Lys Val Gly Asn Ile Glu Tyr
1               5                   10

<210> SEQ ID NO 4
<211> LENGTH: 13
<212> TYPE: PRT
<213> ORGANISM: Homo sapiens

<400> SEQUENCE: 4

Arg Asp Glu Asp Lys Asp Lys Val Gly Asn Val Glu Tyr
1               5                   10

<210> SEQ ID NO 5
<211> LENGTH: 13
<212> TYPE: PRT
<213> ORGANISM: Canis familiaris

<400> SEQUENCE: 5

Lys Glu Arg Gly Glu Phe Asn Asn Glu Arg Gly Glu Arg
1               5                   10

<210> SEQ ID NO 6
<211> LENGTH: 13
<212> TYPE: PRT
<213> ORGANISM: Sus scrofa

<400> SEQUENCE: 6

Lys Glu Arg Gly Glu Tyr Asn Asn Glu Arg Gly Glu Arg
1               5                   10

METHODS OF INHIBITING PLATELET AGGREGATION AND PREVENTING THROMBOSIS USING ANTIBODIES THAT BIND (NA$^+$+K$^+$)-ATPASE BETA SUBUNIT

TECHNICAL FIELD

The invention relates to methods for inhibiting platelet aggregation and to methods for inhibiting and/or preventing thrombosis using antibodies that bind the β subunit of (Na$^+$+K$^+$)-ATPase (NKA).

BACKGROUND OF INVENTION

Thrombosis is the formation of a blood clot (thrombus) which comprises aggregated platelets and a mesh of cross-linked fibrin protein within a blood vessel. A thrombus can restrict blood flow to downstream tissues supplied by the blocked blood vessel. Thrombosis thus deprives the downstream tissue of oxygen and nutrients, and can cause infarction and tissue death. Thrombosis can cause myocardial infarction in the heart when the thrombosis involves a coronary artery supplying the heart, and can cause a stroke when the thrombosis involves a blood vessel in the brain. Depending upon the location of a blot clot within the circulatory system, thrombosis can also cause disease in the kidney, liver, extremities, and other bodily locations.

Antiplatelet medications are most effective at preventing arterial blood clots which are composed largely of platelets. Antiplatelet medications are administered to patients who have coronary artery disease, angina, heart failure, heart valve disease, or at risk for coronary artery disease or stroke, to help prevent a heart attack or stroke.

Thrombosis remains the world's largest single cause of mortality, despite the fact that medication has been available for over 50 years to treat and prevent the condition. Clearly, new treatments for thrombosis are needed.

BRIEF SUMMARY OF INVENTION (Na$^+$+K$^+$)-ATPase (NKA; the sodium pump) is a transmembrane enzyme responsible for the active reciprocal transport of Na$^+$ and K$^+$ ions across the plasma membrane of all animal cells. NKA comprises two basic subunits: the a subunit and the β subunit. The larger a subunit catalyzes the hydrolysis of ATP for active transport of Na$^+$ and K$^+$ ions across the plasma membrane; the smaller β subunit does not participate in the catalytic process of the enzyme, but instead acts as a specific chaperone that assists the biogenesis and correct membrane insertion of newly synthesized NKA.

The present invention is based on the surprising discovery that platelet aggregation can be inhibited using antibodies that bind the β subunit of NKA of platelets. Antibodies with β subunit binding specificity can be used to inhibit platelet aggregation, and inhibit or prevent thrombosis in a subject. Such antibodies thus form the basis of methods of treating or preventing blood clots associated with diseases such as stroke, myocardial infarction, deep vein thrombosis, and generally any venous or arterial thrombosis resulting from platelet aggregation and resulting in patient morbidity or mortality.

Examples of antibodies having β subunit binding specificity that can be used in the methods of the present invention include, but are not limited to, JY2948 and JY421228, humanized versions thereof, and fragments thereof. These antibodies are described in U.S. Pat. Nos. 9,040,046 and 9,527,923, which are herein incorporated by reference in its entirety for all purposes.

In a first aspect, the invention thus provides methods for inhibiting platelet activation comprising contacting platelets with an antibody having binding specificity for the β subunit of NKA. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The method may be conducted in vitro or in vivo. The method may also be conducted in blood ex vivo.

In a second aspect, the invention provides methods for inhibiting platelet aggregation comprising contacting platelets with an antibody having binding specificity for the β subunit of NKA. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The method may be conducted in vitro or in vivo. The method may also be conducted in blood ex vivo.

In a third aspect, the invention provides methods for inhibiting platelet aggregation in a subject comprising administering an effective amount of an antibody having binding specificity for the β subunit of NKA to a subject in need thereof. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a fourth aspect, the invention provides methods for inhibiting thrombosis in a subject comprising administering an effective amount of an antibody having binding specificity for the β subunit of NKA to a subject in need thereof. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is at greater risk than the general population for thrombosis. The subject may be one that is characterized has having or at being at greater risk than the general population for one or more of the following diseases and conditions:

venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a fifth aspect, the invention provides methods for treating thrombosis in a subject comprising administering an effective amount of an antibody having binding specificity for the β subunit of NKA to a subject in need thereof. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a sixth aspect, the invention provides methods for preventing thrombosis in a subject comprising administering an effective amount of an antibody having binding specificity for the β subunit of NKA to a subject in need thereof. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a seventh aspect, the invention provides methods for treating a disease of disregulated platelet aggregation in a subject comprising administering an effective amount of an antibody having binding specificity for the β subunit of NKA to a subject in need thereof. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. Exemplary diseases of dysregulated platelet aggregation include, but are not limited to, hypercoagulability, essential thrombocythemia, reactive thrombocytosis, thrombocytopenia, von Willebrand disease, hereditary intrinsic platelet disorders (e.g., Bernard-Soulier syndrome, May-Hegglin anomaly, Chédiak-Higashi syndrome), and acquired disorders of platelet function (e.g., myeloproliferative and myelodysplastic disorders, uremia, macroglobulinemia, multiple myeloma, cirrhosis).

In an eighth aspect, the invention provides methods for inhibiting thrombosis in a subject comprising administering one or more peptides as vaccine, represented by SEQ ID NOs:1-6, and peptide fragments, derivatives and variants thereof, which peptide is administered in an effective amount that stimulates the immune system to produce (endogenous) antibodies that specifically recognize and bind to the respective peptide epitope (or antigenic site) on the β subunit of the NKA to a subject in need thereof. The subject may one that is at greater risk than the general population for thrombosis. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation. In some embodiments the vector has tissue specific promoters.

In each of these aspects, the antibody or peptide may be in a pharmaceutical formulation comprising the antibody or peptide and a pharmaceutically acceptable carrier.

The foregoing has outlined rather broadly the features and technical advantages of the present invention in order that the detailed description of the invention that follows may be better understood. Additional features and advantages of the invention will be described herein, which form the subject matter of the claims of the invention.

BRIEF DESCRIPTION OF DRAWINGS

FIG. 1A: Isolated platelets+5 µM ADP; FIG. 1B: conditions of 1A+0.2 µM JY2948; FIG. 1C: conditions of 1A+0.2 µM JY421228. All figures have 400× magnification.

FIG. 2A: Human whole blood+5 µM ADP; FIG. 2B: conditions of 2A+0.2 µM JY2948; FIG. 2C: conditions of 2A+0.2 µM JY421228. All figures have 400× magnification.

FIG. 3A-upper curve: Human whole blood+1 µg/ml collagen; FIG. 3A-lower curve: Human whole blood+5 µg/ml collagen. FIG. 3B-upper curve: condition of FIG. 3A-upper curve+0.2 µM JY2948; FIG. 3B-lower curve: condition of FIG. 3A-lower curve+0.2 µM JY2948. FIG. 3C-upper curve: condition of FIG. 3A-upper curve+0.2 µM JY421228. FIG. 3C-lower curve: condition of FIG. 3A-lower curve+0.2 µM JY421228.

FIG. 4A & FIG. 4D: Control background of rat tail before needle stick. FIG. 4B & FIG. 4E: Blood from lateral tail vein after needle stick. FIG. 4C & FIG. 4F: After removal of the blood. FIG. 4G & FIG. 4H: ELISA analyses for generations of endogenous JY2948 (FIG. 4G) or JY421228 (FIG. 4H) antibodies.

DETAILED DESCRIPTION OF THE INVENTION

Figure 1A:
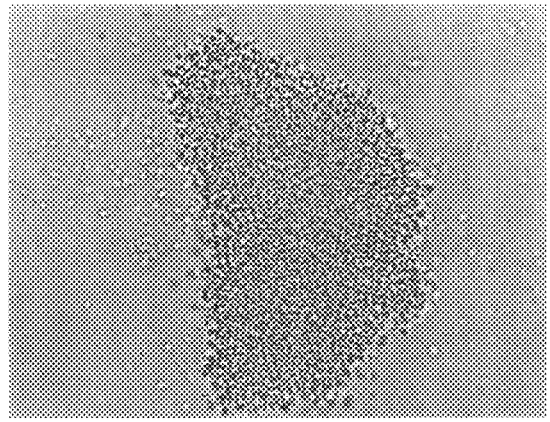
FIGS. 1A-1C. Antibodies JY2948 and JY421228 prevent ADP-induced platelet aggregation in isolated human platelets.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "antibody" generally refers to exogenous or endogenous antibodies. Both exogenous or endogenous antibodies may be generated against SEQ ID NOs:1-4, and peptide fragments, derivatives and variants. These antibodies (i) have binding specificity for the β$_1$ subunit of NKA, (ii) have binding specificity for one or more of the peptides represented by SEQ ID NOs:1-4, and (iii) inhibit platelet aggregation.

As used herein, "peptide" defines an antigenic site or epitopes on the β$_1$ subunit of NKA, which peptide has an amino acid sequence selected from the group comprising SEQ ID NOs:1-4, and fragments, derivatives or variants thereof. The "peptide" and its fragments, derivatives or variants also refer to peptide antigen or vaccine to be used in an amount that stimulates the animal's immune system to produce endogenous antibodies that recognize and bind to the respective peptide epitopes on the β subunit of NKA.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As outlined in a general manner above, the present invention is based on the surprising discovery that platelet aggregation can be inhibited using antibodies (exogenous and endogenous) that bind the β subunit of NKA of platelets. Thus, the β subunit binding-antibodies can be used to inhibit platelet activation and aggregation, whether in vitro or in vivo, to inhibit, treat, and prevent thrombosis in a subject, and to treat a disease of disregulated platelet aggregation in a subject. The antibodies and peptides also form the basis of methods of treating or preventing blood clots associated with diseases such as stroke, myocardial infarction, deep vein thrombosis, and generally any venous or arterial thrombosis resulting from platelet aggregation and resulting in patient morbidity or mortality.

Antibodies

The skilled artisan will understand that the particular attributes of the antibodies (exogenous and endogenous) that may be used in the methods of the present invention are only confined by (i) the ability to bind with specificity to the β subunit of NKA, and (ii) the ability to inhibit platelet aggregation.

As described in US2012/0195886 (U.S. Pat. No. 9,040,046), two antibodies have been prepared that specifically bind the β$_1$ subunit of NKA, namely antibody JY2948 and antibody JY421228. As shown in the Examples below, these antibodies inhibit platelet aggregation and both of them may be used in the methods of the present invention. Antibody JY2948 binds to amino acids 134-146 of the rat β$_1$ subunit of NKA (KERGEFNHERGER; SEQ ID NO:1) and to amino acids 134-146 of the human β$_1$ subunit of NKA (KERGDFNHERGER; SEQ ID NO:2). Antibody JY421228 binds to amino acids 218-230 of the rat β$_1$ subunit of NKA (RDEDKDKVGNIEY; SEQ ID NO:3) and to amino acids 217-229 of the human β$_1$ subunit of NKA (RDEDKDKVGNVEY; SEQ ID NO:4). The invention therefore provides the use of antibody JY2948 and antibody JY421228 in the methods disclosed herein.

The invention also provides the use of antibodies that specifically bind an epitope of the β$_1$ subunit of NKA comprising the amino acid sequence KERGEFNHERGER (SEQ ID NO:1; Rat JY2948 epitope), KERGDFNHERGER (SEQ ID NO:2; Human JY2948 epitope), KERGEFNNERGER (SEQ ID NO:5; Dog JY2948 epitope), KERGEYNNERGER (SEQ ID NO:6; Pig JY2948 epitope), or any combination thereof.

The invention further provides for the use of antibodies having binding specificity for an epitope of the β$_1$ subunit of NKA comprising the amino acid sequence RDEDKDKVGNIEY (SEQ ID NO:3; Rat JY421228 epitope) or RDEDKDKVGNVEY (SEQ ID NO:4; Human JY421228 epitope), or both.

The invention further provides for the use of antibodies having binding specificity for variants of each of the peptides of SEQ ID NOs:1-6, the variants having 5 or fewer, 4 or fewer, 3 or fewer, 2 or fewer, or 1 amino acid change in comparison to the peptides of SEQ ID NOs:1-6. The changes are each individually selected from insertions, deletions and substitutions. The substitutions may be conservative or non-conservative amino acid substitutions. Each of the variant peptides maintains the ability to induce production of antibodies that specifically bind the β subunit of NKA and that have the ability to inhibit platelet aggregation.

In addition, the invention provides for the use of antibodies having binding specificity for other epitopes of the β subunit of NKA, with those antibodies having binding specificity for other epitopes of the $β_1$ subunit of NKA being of particular note.

The antibodies used in the methods of the present invention and defined above may be polyclonal, monoclonal, humanized or chimeric antibodies, and the antibodies may be in the form of an antiserum comprising the antibodies. The antibodies may be of any class, such as IgG1, IgG2, IgG3, IgG4, IgM, IgA1, IgA2, IgD or IgE. The antibodies may be isolated antibodies, purified antibodies, exogenous antibodies, endogenous antibodies, or a combination thereof.

The antibodies may also be antibody fragments of less than the entire antibody, including, but not limited to, single chain antibodies, F(ab')$_2$ fragments, Fab fragments, and fragments produced by an Fab expression library, and derivatives of the antibodies and fragments defined herein, with the only limitation being that the antibody fragments and derivatives retain the ability to bind the β subunit and aggregate platelets. It will thus be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more of the peptides or variants discussed herein. The peptides and variants may be administered in conjunction with one or more pharmaceutically acceptable adjuvants to increase the immunological response. Suitable adjuvants include, but are not limited to, Freund's Complete and Incomplete Adjuvant, Titermax, Oil in Water Adjuvants, as well as Aluminum compounds where antigens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the peptide and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)). Each of these publications are herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety. Methods for making, isolating and purifying antibodies and the above-identified peptide antigenic determinants are described in U.S. Patent Applications 20040057956 and 20030228315, the entire contents of which are hereby incorporated by reference as if fully set forth herein.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Chimeric antibodies are those where an antigen binding region (e.g., F(ab')2 or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci* 81:6851-6855 (1984); Neuberger et al., *Nature* 312:604-608(1984); Takeda et al., *Nature* 314:452-454 (1985), each of which is herein incorporated by reference in its entirety.

Techniques for the production of single chain antibodies are described in U.S. Pat. No. 4,946,778, incorporated herein by reference in its entirety.

Antibody fragments such as F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

The invention provides for the use of pharmaceutical formulations comprising one or more of the antibodies of the invention and a pharmaceutically acceptable carrier. Such formulations may be administered to a subject when practicing the methods of the present invention. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The identity of the carrier(s) will also depend on the means used to administer pharmaceutical formulations comprising antibodies to a subject. For example, pharmaceutical formulations for intramuscular preparations can be prepared where the carrier is water-for-injection, 0.9% saline, or 5% glucose solution. Pharmaceutical formulations may also be prepared as liquid or powdered atomized dispersions for delivery by inhalation. Such dispersion typically contain carriers common for atomized or aerosolized dispersions, such as buffered saline and/or other compounds well known to those of skill in the art. The delivery of the pharmaceutical formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the pharmaceutical formulations may also be administered in a liquid form. The liquid can be for oral dosage, for ophthalmic or nasal dosage as drops, or for use as an enema or douche. When the pharmaceutical formulation is formulated as a liquid, the liquid can be either a solution or a suspension of the pharmaceutical formulation. There is a variety of suitable formulations for the solution or suspension of the pharmaceutical formulations that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

Methods for Inhibiting Platelet Aggregation

As indicated above, the present invention includes methods for inhibiting platelet aggregation. This method comprising contacting platelets with an antibody having binding specificity for the β subunit of NKA. It will be apparent to the skilled artisan that this method can be practice in vitro, in vivo and ex vivo (e.g., in blood flowing through a heart bypass machine during surgery).

Any of the antibodies (exogenous or endogenous) described herein, whether polyclonal or monoclonal, can be used in the method, as well as humanized or chimeric versions of the antibodies, and fragments of any of these. Exemplary antibodies that may be used in these methods include, but are not limited to, (i) antibodies having binding specificity for the $\beta_1$ subunit of NKA, (ii) antibodies having binding specificity for one or more of the peptides represented by SEQ ID NOs:1-4, (iii) antibody JY421228 or a humanized version thereof, and (iv) antibody JY2948 or a humanized version thereof.

Methods for Inhibiting Platelet Activation

The present invention includes methods for inhibiting platelet activation. This method comprising contacting platelets with an antibody having binding specificity for the β subunit of NKA. It will be apparent to the skilled artisan that this method can be practice in vitro, in vivo and ex vivo (e.g., in blood flowing through a heart bypass machine during surgery). Any of the antibodies described herein, whether polyclonal or monoclonal, can be used in the method, as well as humanized or chimeric versions of the antibodies, and fragments of any of these. Exemplary antibodies that may be used in these methods include, but are not limited to, (i) antibodies having binding specificity for the $\beta_1$ subunit of NKA, (ii) antibodies having binding specificity for one or more of the peptides represented by SEQ ID NOs:1-4, (iii) antibody JY421228 or a humanized version thereof, and (iv) antibody JY2948 or a humanized version thereof.

Methods of Treatment

The invention also provides methods for treating or preventing particular diseases, disorders and conditions in a subject by inhibiting platelet aggregation.

The invention thus includes methods for inhibiting platelet aggregation in a subject comprising administering an effective amount of an antibody having binding specificity for the β subunit of NKA to a subject in need thereof. While the subject is not limited to one having a particular disease or condition, the subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, myocardial infarction, and post-surgical thrombotic complications arising from angioplasty and organ transplantation or other disease or condition wherein inhibition of platelet aggregation would be desirable or necessary.

The invention includes methods for inhibiting, treating or preventing thrombosis in a subject, where the method comprises administering an effective amount of an antibody having binding specificity for the β subunit of NKA to a subject in need thereof. While the subject is not limited to one having a particular disease or condition, the subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, myocardial infarction, and post-surgical thrombotic complications arising from angioplasty and organ transplantation or other disease or condition wherein inhibition of platelet aggregation would be desirable or necessary.

The invention also includes methods for treating a disease of disregulated platelet aggregation in a subject comprising administering an effective amount of an antibody having binding specificity for the β subunit of NKA to a subject in need thereof. Exemplary diseases of dysregulated platelet aggregation include, but are not limited to, hypercoagulability, essential thrombocythemia, reactive thrombocytosis, thrombocytopenia, von Willebrand disease, hereditary intrinsic platelet disorders (e.g., Bernard-Soulier syndrome, May-Hegglin anomaly, Chédiak-Higashi syndrome), and acquired disorders of platelet function (e.g., myeloproliferative and myelodysplastic disorders, uremia, macroglobulinemia, multiple myeloma, cirrhosis).

Any of the antibodies (exogonous or endogenous) described herein, whether polyclonal or monoclonal, can be used in the method, as well as humanized or chimeric versions of the antibodies, and fragments and derivatives of any of these. Exemplary antibodies that may be used in these methods include, but are not limited to, (i) antibodies having binding specificity for the $\beta_1$ subunit of NKA, including isoform of $\beta_1$ subunit, (ii) antibodies having binding specificity for one or more of the peptides represented by SEQ ID NOs:1-6, (iii) antibody JY421228 or a humanized version thereof, or a fragment or derivative thereof, and (iv) antibody JY2948 or a humanized version thereof, or a fragment or derivative thereof. The antibody may be administered as a pharmaceutical formulation comprising the antibody and a pharmaceutically acceptable carrier.

As used herein, the terms "treat", "treating" and "treatment" have their ordinary and customary meanings, and include one or more of, ameliorating thrombosis or a disease of dysregulated platelet aggregation, ameliorating a symptom of thrombosis or a disease of dysregulated platelet aggregation, or decreasing in severity and/or frequency a symptom of thrombosis or a disease of dysregulated platelet aggregation. Treatment means ameliorating or decreasing by about 1% to about 100% versus a subject to which the antibody has not been administered. Preferably, the ameliorating or decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of thrombosis or a disease of dysregulated platelet aggregation. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "prevent", "preventing" and "prevention" have their ordinary and customary meanings, and include one or more of, stopping, averting, avoiding or blocking thrombosis, the occurrence of a symptom of thrombosis, the recurrence of a symptom of thrombosis, the development of thrombosis or the progression of thrombosis. Prevention means stopping by at least about 95% versus a subject to which the antibody has not been administered. Preferably, the stopping is about 100%, about 99%, about 98%, about 97%, about 96% or about 95%. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "inhibit", "inhibiting" and "inhibition" have their ordinary and customary meanings, and include one or more of, hindering, impeding, obstructing, deterring or restraining platelet aggregation or thrombosis, the occurrence of a symptom of platelet aggregation or thrombosis, the recurrence of a symptom of platelet aggregation or thrombosis, the development of platelet aggregation or thrombosis, or the progression of platelet aggregation or thrombosis. Inhibition means impeding by about 1% to about 100% versus a subject to which the antibody has not been administered. Preferably, the impeding is about 100%, about 99%, about 98%, about 97%, about 96%, about 95%, about 90%, about 80%, about 70%, about 60%, about 50%, about 40%, about 30%, about 20%, about 10%, about 5% or about 1%. The course of therapy may begin prior to, concurrent with, or after the onset of clinical symptoms of platelet aggregation or thrombosis. Thus, the subject may have platelet aggregation or thrombosis, or merely be susceptible to platelet aggregation or thrombosis. The results of the inhibition may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The antibodies and formulations may be administered to a subject using different schedules, depending on the particular aim or goal of the method; the age and size of the subject; and the general health of the subject, to name only a few factors to be considered. In general, the antibodies and formulations may be administered once, or twice, three times, four times, five times, six times or more, over a course of treatment, inhibition or prevention. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of antibody may be administered in each dose of the dosing schedule, or the amounts in each dose may vary. The identity of the particular antibody may also vary or remain the same in each dose in a dosing schedule.

In each of the methods of the present invention, an "effective amount" of an antibody or peptide or a pharmaceutical formulation comprising an antibody or peptide is administered to a subject. The effective amount will vary between subjects. However, the effective amount is one that is sufficient to achieve the aim or goal of the method, whether inhibiting, treating or preventing. As an example, an effective amount of an antibody used in the methods of the invention is typically between about 0.1 µg to about 1000 µg of antibody per kg of body weight of the subject to which the antibody is administered. An effective amount also includes between about 1 µg to about 500 µg, between about 10 µg to about 200 µg, between about 1 µg to about 800 µg, between about 10 µg to about 800 µg, between about 1 µg to about 300 µg, and between about 10 µg to about 300 µg of antibody per kg of body weight of the subject.

Appropriate doses and dosing schedules can readily be determined by techniques well known to those of ordinary skill in the art without undue experimentation. Such a determination will be based, in part, on the tolerability and efficacy of a particular dose.

Administration of the antibody or formulation may be via any of the means commonly known in the art of antibody delivery. Such routes include intravenous, intraperitoneal, intramuscular, subcutaneous and intradermal routes of administration, as well as nasal application, by inhalation, ophthalmically, orally, rectally, vaginally, or by any other mode that results in the antibody or formulation contacting mucosal tissues.

The term "subject" is intended to mean an animal, such birds or mammals, including humans and animals of veterinary or agricultural importance, such as dogs, cats, horses, sheep, goats, and cattle.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

"Recombinant," as applied to a polynucleotide, means that the polynucleotide is the product of various combinations of cloning, restriction and/or ligation steps, and other procedures that result in a construct that is distinct from a polynucleotide found in nature.

A "gene" refers to a polynucleotide or portion of a polynucleotide comprising a sequence that encodes a protein. For most situations, it is desirable for the gene to also comprise a promoter operably linked to the coding sequence in order to effectively promote transcription. Enhancers, repressors and other regulatory sequences may also be included in order to modulate activity of the gene, as is well known in the art. (See, e.g., the references cited below).

The terms "polypeptide," "peptide," and "protein" are used interchangeably to refer to polymers of amino acids of any length, or derivatives. These terms also include proteins that are post-translationally modified through reactions that include glycosylation, acetylation and phosphorylation.

Peptide "fragment" means any fragment or portion of the peptide.

The terms "variant" and "amino acid sequence variant" are used interchangeably and designate polypeptides in which one or more amino acids are added and/or substituted and/or deleted and/or inserted at the N- or C-terminus or anywhere within the corresponding native sequences used herein, the term "variant" is interpreted to mean a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

The terms "derivatizing" and "derivative" or "derivatized" include processes and all resulting peptides or modified peptides, respectively. Including those in which (1) the peptide or modified peptide has a cyclic portion; for example, cross-linking between cysteinyl residues within the modified peptide; (2) the peptide or modified peptide is cross-linked or has a cross-linking site; for example, the peptide or modified peptide has a cysteinyl residue and thus forms cross-linked dimers in culture or in vivo; (3) one or more peptidyl linkage is replaced by a non-peptidyl linkage; (4) the N-terminus is replaced by —NRR.sup.1, NRC(O)R.sup.1, —NRC(O)OR.sup.1, —NRS(O).sub.2 R.sup.1, —NHC(O)NHR, a succinimide group, or substituted or unsubstituted benzyloxycarbonyl-NH—, wherein R and R.sup.1 and the ring substituents are as defined hereinafter; (5) the C-terminus is replaced by —C(O)R.sup.2 or —NR.sup.3 R.sup.4 wherein R.sup.2, R.sup.3 and R.sup.4 are as defined hereinafter; and (6) peptides or modified peptides in which individual amino acid moieties are modified through treatment with agents capable of reacting with selected side chains or terminal residues.

An "effective amount" is an amount sufficient to effect beneficial or desired clinical results. An effective amount can be administered in one or more administrations. The antibodies, peptides or vectors used as vaccines of the present invention can be administered to a patient at therapeutically effective doses to treat (including prevention) heart disease and/or other muscular contractile disorders. A therapeutically effective dose refers to that amount of the compound sufficient to result in desired treatment. As used herein, the term "antibody or antibodies" includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library. "Antibody" refers to a polypeptide ligand substantially encoded by an immunoglobulin gene or immunoglobulin genes, or fragments thereof, which specifically binds and recognizes an epitope (e.g., an antigen). The recognized immunoglobulin—genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'.sub.2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, CH, CH.sub.2 and CH.sub.3, but does not include the heavy chain variable region.

As used herein, the term "fragment", as applied to an antibody means any fragment of the antibody that includes the antigenic determinant/epitope to which the complete antibody binds, including Fab, Fab', F(ab)$_2$, and F(ab')$_2$ fragments. As applied to a peptide means any fragment of a peptide from SEQ ID NOS: 1-6.

As used herein, the term "substantially pure or purified" describes a compound (e.g., a protein or polypeptide) which has been separated from components which naturally accompany it. Typically, a compound is substantially pure when at least 10%, more preferably at least 20%, more preferably at least 50%, more preferably at least 60%, more preferably at least 75%, more preferably at least 90%, and even more preferably at least 99%, of the total material (by volume, by wet or dry weight, or by mole percent or mole fraction) in a sample is the compound of interest. Purity can be measured by any appropriate method. In the case of polypeptides, for example, purity can be measured by column chromatography, polyacrylamide gel electrophoresis, or HPLC analysis. A compound such as a protein is also substantially purified when it is essentially free of naturally associated components or when it is separated from the native contaminants which accompany it in its natural state.

A "substantially pure nucleic acid or purified", as used herein, refers to a nucleic acid sequence, segment, or fragment which has been purified from the sequences which flank it in a naturally occurring state, e.g., a DNA fragment which has been removed from the sequences which are normally adjacent to the fragment such as the sequences adjacent to the fragment in a genome in which it naturally occurs. The term also applies to nucleic acids which have been substantially purified from other components which naturally accompany the nucleic acid, e.g., RNA or DNA, which has been purified from proteins which naturally accompany it in the cell.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. "Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

A "replicon" refers to a polynucleotide comprising an origin of replication which allows for replication of the polynucleotide in an appropriate host cell. Examples include replicons of a target cell into which a heterologous nucleic acid might be integrated (e.g., nuclear and mitochondrial chromosomes), as well as extrachromosomal replicons (such as replicating plasmids and episomes).

In accordance with the invention, the antibodies of the invention are also used as diagnostic agents which detect muscle contractile disorders, especially, for example, in the heart. In one embodiment, any of the above-described molecules can be labeled, either detectably, as with a radioisotope, a paramagnetic atom, a fluorescent moiety, an enzyme, etc. in order to facilitate its detection in, for example, in situ or in vivo assays. The molecules may be labeled with reagents such as biotin, in order to, for example, facilitate their recovery, and/or detection.

As used herein, an "antigenic determinant" is the portion of an antigen molecule that determines the specificity of the antigen-antibody reaction. An "epitope" also refers to an antigenic determinant of a polypeptide and is used interchangeably herein. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. Proc. Natl. Acad. Sci. U.S.A. 81:3998-4002; PCT Publication No. WO 84/03564; and PCT Publication No. WO 84/03506.

Actual methods for preparing parenterally administrable compositions and adjustments necessary for administration to subjects will be known or apparent to those skilled in the art and are described in more detail in, for example, Remington's Pharmaceutical Science, 15th Ed., Mack Publishing Company, Easton, Pa. (1980), which is incorporated herein by reference.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin Remington's Pharm. Sci., 15th Ed. (Mack Publ. Co., Easton (1975).

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED.50. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The invention also provides for vectors which are used for treating a patient suffering from or susceptible heart disease. As used herein, a "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available (see, e.g., the various references cited below).

As used herein, the term "administering a molecule to a cell" (e.g., an expression vector, nucleic acid, peptide, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell). This term is to be distinguished from administering a composition to a patient.

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

A "recombinant viral vector" refers to a viral vector comprising one or more heterologous genes or sequences. Since many viral vectors exhibit size-constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation) (see, e.g., the references and illustrations below). Modified viral vectors in which a polynucleotide to be delivered is carried on the outside of the viral particle have also been described (see, e.g., Curiel, D T, et al. PNAS 88: 8850-8854, 1991).

Viral "packaging" as used herein refers to a series of intracellular events that results in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" genes, found in many viral genomes, are genes encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain genes encoding the missing functions which can be supplied in trans). For example, such packaging genes can be stably integrated into a replicon of the packaging cell line or they can be introduced by transfection with a "packaging plasmid" or helper virus carrying genes encoding the missing functions.

A "detectable marker gene" is a gene that allows cells carrying the gene to be specifically detected (e.g., distinguished from cells which do not carry the marker gene). A large variety of such marker genes are known in the art. Preferred examples thereof include detectable marker genes which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining, as described below.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., WO 92/08796, published May 29, 1992, and WO 94/28143, published Dec. 8, 1994). Such marker genes can provide an added measure of control that can be advantageous in gene therapy contexts. "Treatment" or "therapy" as used herein also refers to administering, to an individual patient, agents that are capable of eliciting a prophylactic, curative or other beneficial effect in the individual.

"Gene therapy" as used herein refers to administering, to an individual patient, vectors comprising a therapeutic gene, such as the vectors carrying one or more of the peptides from SEQ ID NOs: 1-6, or to fragments, derivatives or variants thereof.

A "therapeutic polynucleotide" or "therapeutic gene" refers to a nucleotide sequence that is capable, when transferred to an individual, of eliciting a prophylactic, curative or other beneficial effect in the individual. Such as expressing one or more of the peptide antigenic epitopes described herein which in turn elicit an immune response from the host.

The practice of the present invention can suitably employ, unless otherwise indicated, conventional techniques of molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W. B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

Preferred vectors for use in the present invention include viral vectors, lipid-based vectors and other vectors that are capable of delivering DNA to non-dividing cells in vivo. Presently preferred are viral vectors, particularly replication-defective viral vectors (including, for example replication-defective adenovirus vectors and adeno-associated virus (AAV) vectors. For ease of production and use in the present invention, replication-defective adenovirus vectors are presently most preferred.

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein. Targeted vectors include vectors (such as viruses, non-viral protein-based vectors and lipid-based vectors) in which delivery results in transgene expression that is relatively limited to particular host cells or host cell types. By way of illustration, therapeutic molecules, for example, nucleic acid sequences encoding for the peptides of the invention, to be delivered to a patient can be operably linked to heterologous tissue-specific promoters thereby restricting expression to cells in that particular tissue.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

When vectors are used to express peptide epitopes for example to stimulate production of antibody for use in treating or preventing thrombosis, they are sometimes administered systemically. Other times they are administered locally for example by injection into a blood vessel directly supplying the target tissue. For example, if it is the heart, then they are injected into a vessel supplying the myocardium, preferably by injection into a coronary artery. Such injection is preferably achieved by catheter introduced substantially (typically at least about 1 cm) within the ostium of one or both coronary arteries or one or more saphenous veins or internal mammary artery grafts or other conduits delivering blood to the myocardium. By injecting the vector stock, preferably containing no wild-type virus, deeply into the lumen of an artery (or grafts and other vascular conduits), and preferably in an amount of about $10^{7-13}$ viral particles as determined by optical densitometry (more preferably $10^{9-11}$ viral particles), it is possible to locally transfect a desired number of cells with genes that encode proteins that regulate cell NKA, such as, for example, the peptides discussed herein. This maximizes the therapeutic efficacy of gene transfer, and minimizes undesirable effects at other sites such as the possibility of an inflammatory response to viral proteins. For example, vector constructs that are specifically targeted to the myocardium, such as vectors incorporating myocardial-specific binding or uptake components, and/or which incorporate inotropic molecules, for example, the peptides described above, that are under the control of myocardial-specific transcriptional regulatory sequences (e.g., ventricular myocyte-specific promoters) can be used in place of or, preferably, in addition to such directed injection techniques as a means of further restricting expression to the myocardium, especially the ventricular myocytes. For vectors that can elicit an immune response, it is preferable to inject the vector directly into a blood vessel supplying the targeted cells or tissue, although the additional techniques for restricting the potential for non-target expression can also be employed.

A kit comprising the necessary components for practicing the methods of the invention, including an antibody or a pharmaceutical formulation comprising an antibody, and instructions for its use is also within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

Examples

Inhibition of ADP-Induced Platelet Activation and Aggregation

Materials: ZEISS Axioskop microscope, Micro cover glass, Microscope slides, 1 mM ADP, human blood, and isolated human platelets. Method-1: Preparation of platelet-rich plasma (PRP): Human blood was collected from a healthy volunteer who was not on any medications. PRP was prepared by centrifuging blood at 100 g for 20 min at room temperature (with no brake applied) using a Sonvall Legend X1R centrifuge (Thermo Scienfific). After the spin, three distinct layers were observed. The top straw-colored layer was used as PRP. Method-2: Detection of ADP induced platelet aggregation: Fresh-made PRP (FIG. 1A-1C) or whole blood (FIG. 2A-2C) were incubated with or without antibody JY2948 or JY421228 for 60 minutes at room temperature followed by addition of 0.2 µM ADP. Experimental sample (10 µl each) was taken from the reaction mixture on to a microscope slide and covered by a micro cover glass. Platelet aggregation and the prevention of its aggregation were detected by a ZEISS Axioskop microscope.

Figure 1B:
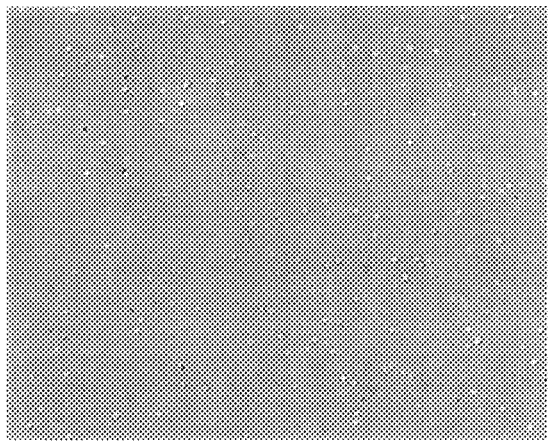
Figure 1C:
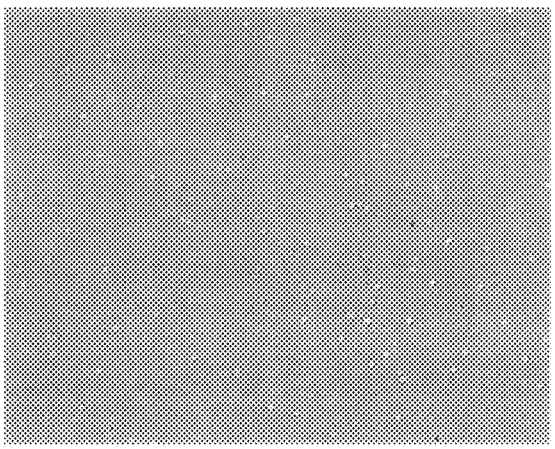
Figure 2A:
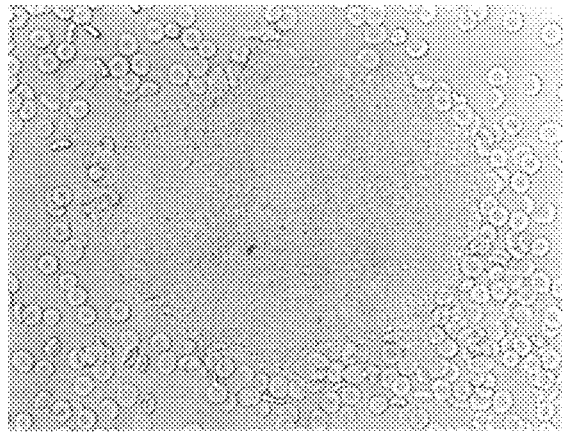
FIGS. 2A-2C. Antibodies JY2948 and JY421228 prevent ADP-induced platelet aggregation in whole blood.
Figure 2B:
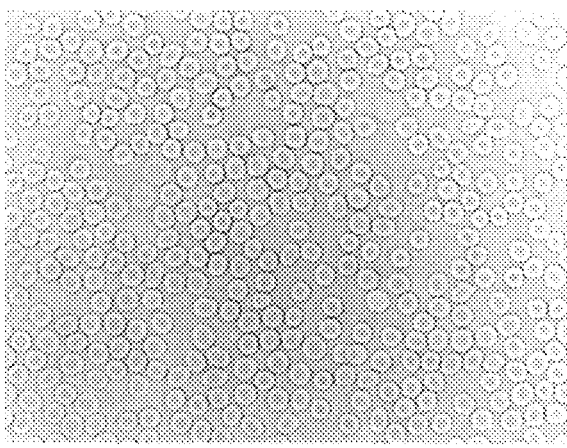
Figure 2C:
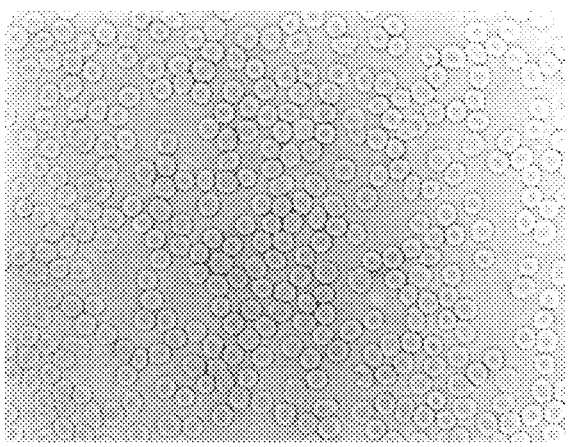

As shown in FIG. 1A, 5 µM ADP induced activation and aggregation in an isolated culture of human platelets. In distinct contrast, 0.2 µM mAb JY2948 (FIG. 1B) or mAb JY421228 (FIG. 1C) prevented platelet activation and aggregation in the presence of ADP. Similar results were found when testing on human whole blood level, ADP induced platelet activation and aggregation as shown in FIG. 2A and both JY2948 (FIG. 2B) and JY421228 (FIG. 2C) prevented the formation of platelet aggregation.

Platelet Inhibition in the Presence of Collagen

Materials: Aggregometer (Chrono-Log Corporation), isotonic saline, collagen (1 mg/ml), and human blood. Method: Impedance measurement: Electrical impedance aggregation measurements were performed on an aggregometer (Chrono-Log Corporation, 560 model), which was equipped with automated calibration and readout functions. The instrument was maintained according to the manufacturer instructions for proper cleaning and maintenance of the electrode. The blood sample (0.5 mL each) was incubated with or without antibody JY2948 or JY421228 (0.2 µM) for 60 minutes at room temperature prior to be diluted with an equivalent volume of isotonic saline and incubated for 5 minutes at 37° C. The impedance of each sample was monitored in sequential 1-minute intervals until a stable baseline was established. After a stable baseline was established, the collagen was added to the sample, aggregation was monitored for approximately 8-11 minutes, and the final increase in ohms over this period was displayed as a numeric LED readout. In addition, a graphical printout (i.e., chart tracing) of each electrical impedance aggregometry tracing was obtained.

Figure 3A:
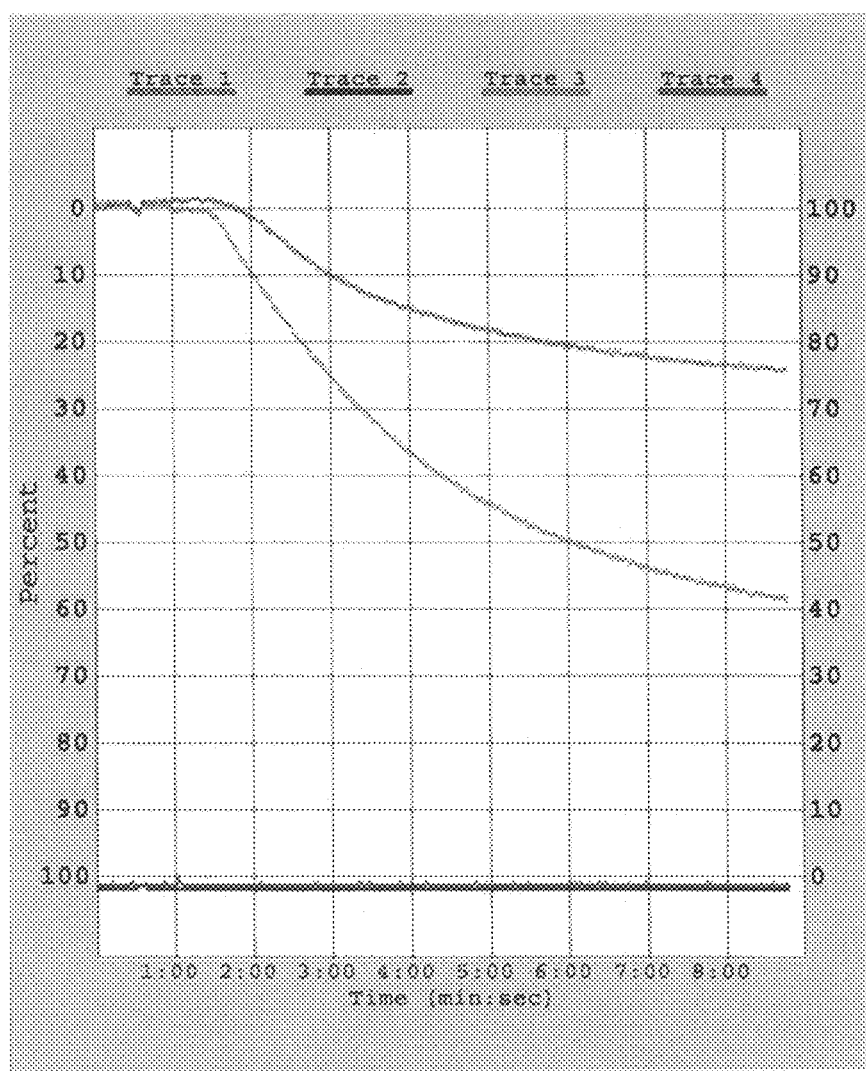
FIGS. 3A-3C. Antibodies JY2948 and JY421228 prevent platelet aggregation in the presence of collagen.
Figure 3B:
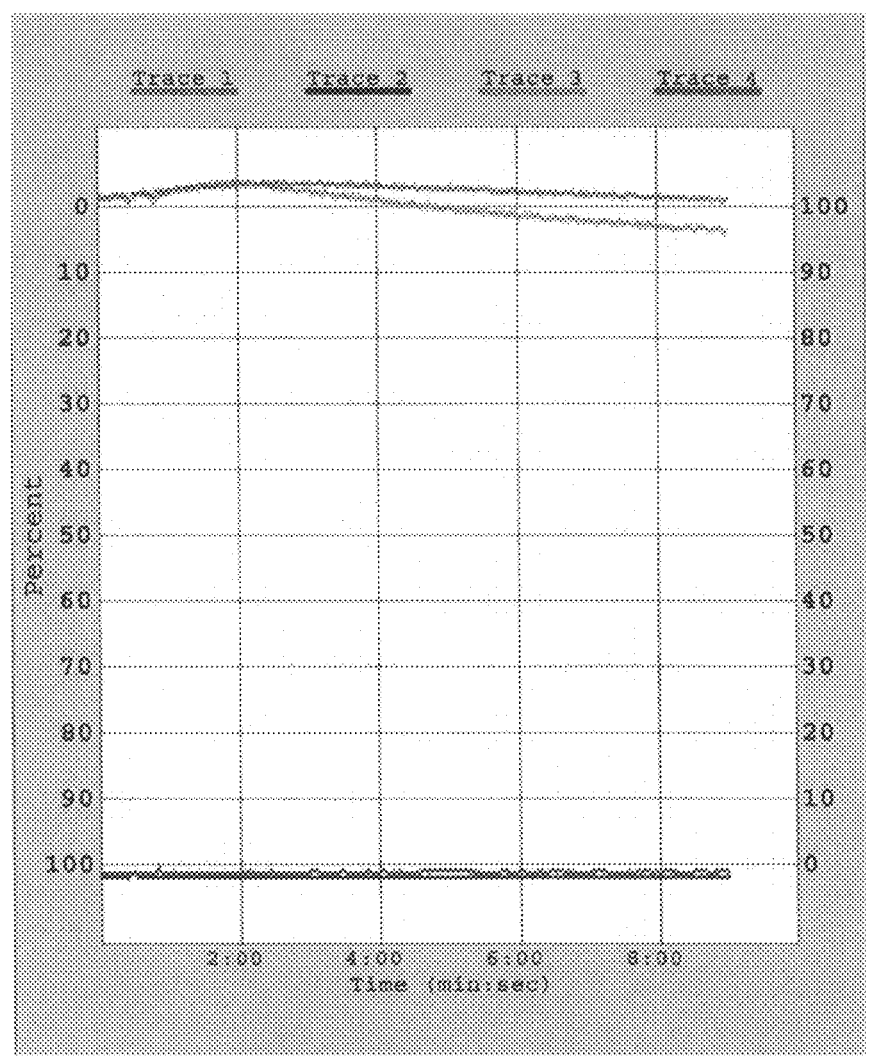
Figure 3C:
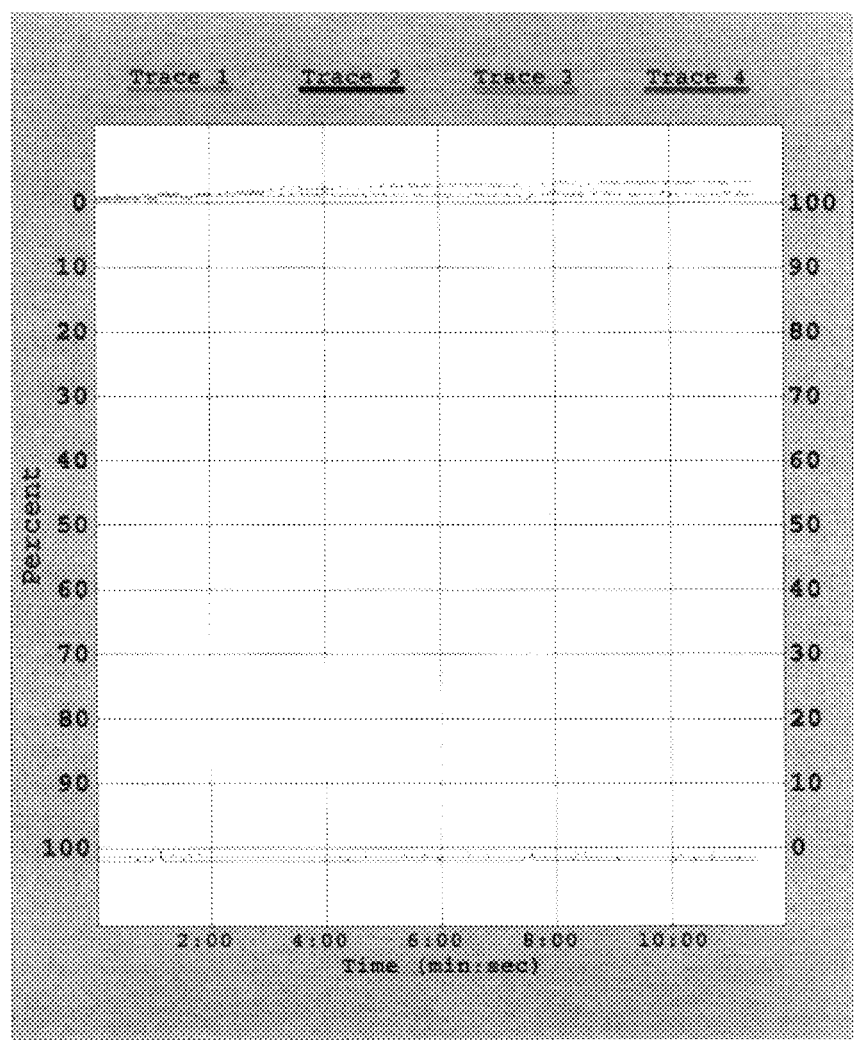

As shown in FIG. 3A, both 1 (upper curve) and 5 (lower curve) µg/ml collagen induced platelet aggregation. However, JY2948 (FIG. 3B) and JY421228 (FIG. 3C) (0.2 µM each) significantly inhibited platelet activation and aggregation, demonstrating that both JY2948 and JY421228 antibodies have the capability to prevent platelet aggregation, which may be potentially used to prevent and treat thrombosis and its associated disorders, including stroke, myocardial infarction and pulmonary embolism.

Bleeding Tests

Figures 4A, 4B, 4C, 4D, 4E, 4F:
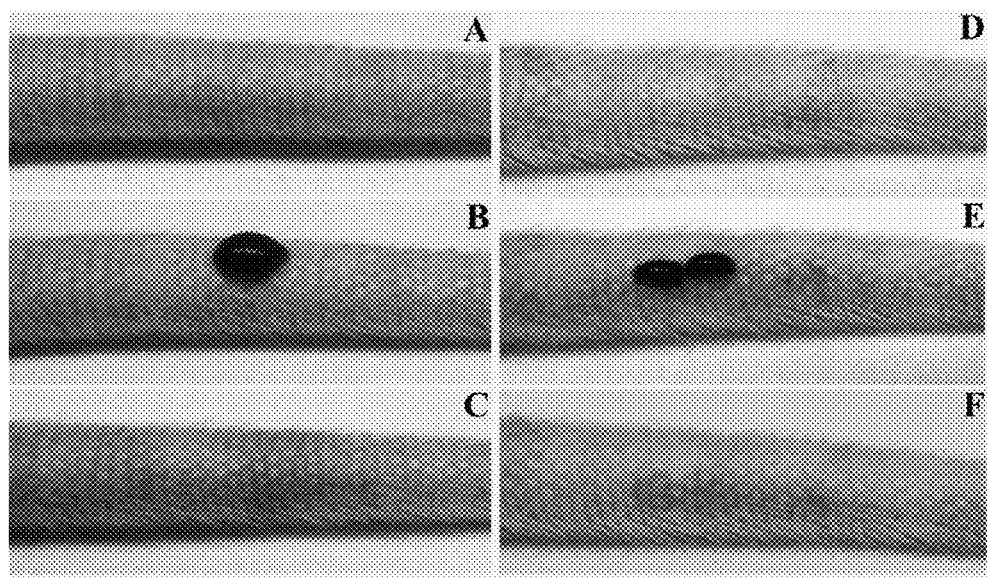
FIGS. 4A-4H. Antibodies JY2948 and JY421228 do not cause bleeding (n=5/each group). Representative Rat 1 (FIG. 4A, FIG. 4B & FIG. 4C) and Rat 2 (FIG. 4D, FIG. 4E & FIG. 4F) were immunized with antigen of JY2948 and JY421228, respectively. A quick bleeding test was performed at rat lateral tail vein.
Figures 4G, 4H:
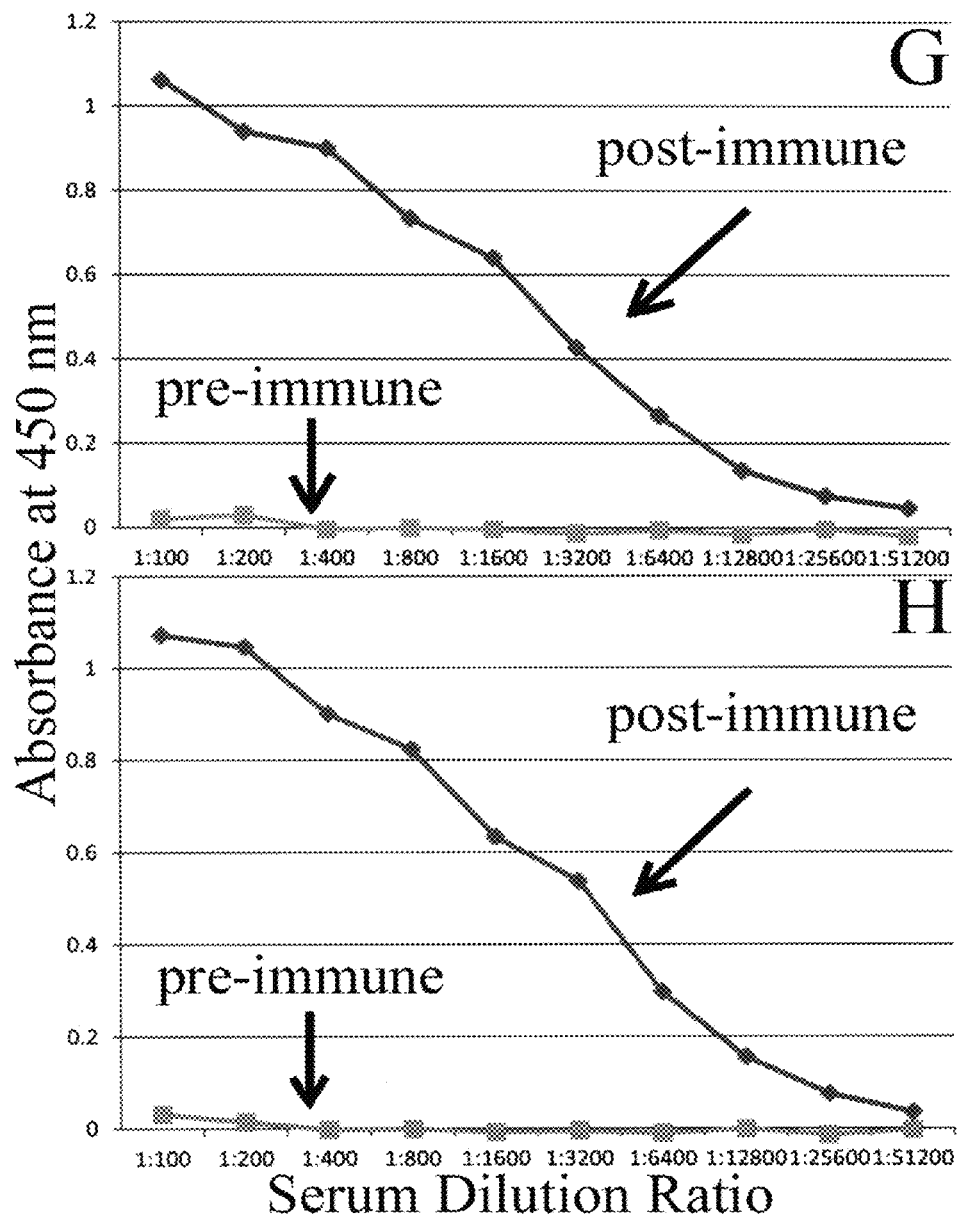

Rats were immunized with antigen JY2948 (KERGEFN-HERGER; SEQ ID NO:1) or JY421228 (RDEDKDK-VGNIEY; SEQ ID NO:3) separately for two months. ELISA assay analyses demonstrated the generation of JY2948 antibody with an antibody titer over 1:4800 (FIG. 4G) and JY421228 antibody with an antibody titer over 1:6400 (FIG. 4H).

A bleeding test was performed at the rat lateral tail vein. Representative Rat 1 (FIGS. 4A-4C) and Rat 2 (FIGS. 4D-4F) immunized with antigen JY2948 and JY421228, respectively. FIGS. 4A & 4D: Control background of rat tail before needle stick. FIGS. 4B & 4E: Blood from lateral tail vein after needle stick. FIGS. 4C & 4F: After removal of the blood. Time length of the bleeding test from beginning and finish was 5-6 seconds. Five Rats were used per each group and all rats had similar results. Antibodies JY2948 and JY421228 were thus found to not increase bleeding in experimental animals.

Animal In Vivo Anti-Thrombosis Test

Figures 5A, 5B:
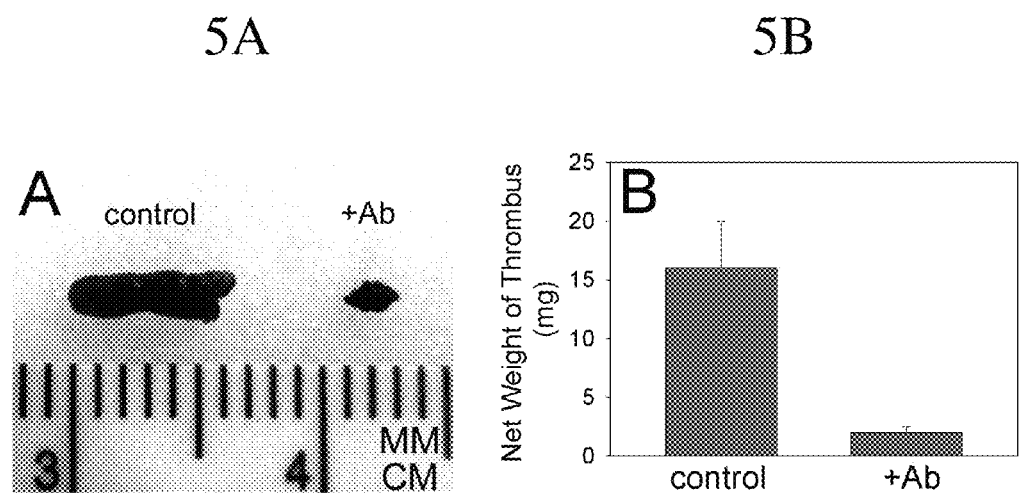
FIGS. 5A-5B. Representative in vivo anti-thrombosis effect of endogenous JY2948 antibody on mouse model of deep venous thrombosis. Mice were immunized with synthetic peptide SEQ ID NO: 1 conjugated with protein carrier KLH as vaccine (0.05 mg/mouse) to generate endogenous JY2948 antibody in mice prior to surgical ligation inferior vena cava (IVC) stasis model in the absence of blood flow. 5A: Ligation of IVC causes thrombus formation in the absence (left: control) and presence (right: +Ab) of endogenous JY2948 antibody. 5B: Thrombus was weighted and the net weight of the thrombus was shown in 5B. The experimental results show that absence of JY2948 caused a 16 mg thrombus formation, which is 8 fold of the thrombus formed in the presence of JY2948. These data provide animal in vivo evidence to demonstrate that endogenous antibody JY2948 has anti-thrombosis effect (n=4).

Representative an animal in vivo anti-thrombosis test was performed in a well-established and widely used mouse stasis animal model of deep venous thrombosis (DVT) involves a total occlusion or ligation of the IVC complete blood stasis (Brill A, et al. Blood, 2011, vol 117, page 1400-1407; Myers D Jr, et al. J Surg Res, 2002, vol 108, page 212-221; Day S M, et al. Thromb Haemost, 2004, vol 92, page 486-494). FIGS. 5A and 5B show that absence of blood flow caused a 16 mg thrombus formation, which is 8 fold of the thrombus formed in the presence of endogenous JY2948 generated by peptide vaccine. Four mice were used per each group and all mice had similar results under each experimental condition. The data provide animal in vivo evidence to demonstrate that endogenous antibody JY2948 has anti-thrombosis effect (n=4).

Antibody Involvement in Conventional Drug Pathways

Table 1 illustrates that antibodies JY2948 and JY421228 do not participate in any of the conventional drug pathways and suggests the basis as to why antibodies JY2948 and JY421228 do not cause bleeding.

| Drug Name | Irreversible Binding | Inhibition of Clotting Factors | Inhibition of Forming Thrombin | Inhibition of IIB/IIIa Pathways |
|---|---|---|---|---|
| Aspirin | Yes | | | |
| Clopidogrel | Yes | | | |
| Abciximab | Yes | | | |
| Coumarins | | Yes | | |
| Hirudin | | | Yes | |
| Argatroban | | | Yes | |
| Tirofiban | | | | Yes |
| Eptifibatide | | | | Yes |
| JY2948, JY421228 | No | No | No | No |

What is claimed is:

1. A method of inhibiting thrombosis in a subject comprising administering a pharmaceutically effective synthetic peptide vaccine to a subject in need thereof, wherein said peptide vaccine comprises a synthetic peptide selected from SEQ ID NOS: 1-6 and a pharmaceutically acceptable carrier, wherein said peptide vaccine stimulates the host immune system to generate endogenous antibodies that specifically bind to the β1 subunit of the $(Na^++K^+)$-ATPase.

2. The method of claim 1, wherein the subject has or is at greater risk than the general population for a disease or condition selected from the group consisting of venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

* * * * *